(12) United States Patent  
Schöb

(10) Patent No.: US 6,637,433 B2  
(45) Date of Patent: Oct. 28, 2003

(54) GAS FORWARDING APPARATUS FOR RESPIRATION AND NARCOSIS DEVICES

(75) Inventor: Reto Schöb, Volketswil (CH)

(73) Assignee: Levitronix LLC, Waltham, MA (US)

( * ) Notice: Subject to any disclaimer, the term of this patent is extended or adjusted under 35 U.S.C. 154(b) by 0 days.

(21) Appl. No.: 09/872,388

(22) Filed: May 31, 2001

(65) Prior Publication Data

US 2002/0000228 A1 Jan. 3, 2002

(30) Foreign Application Priority Data

Jun. 26, 2000 (EP) .............................. 00810558

(51) Int. Cl.$^7$ .............................................. A61M 16/00
(52) U.S. Cl. .............................. 128/204.19; 128/205.18
(58) Field of Search ................... 128/204.19, 204.18, 128/205.18, 203.12, 203.14

(56) References Cited

U.S. PATENT DOCUMENTS 3,107,310 A  10/1963  Carriere 5,906,203 A  5/1999  Klockseth

FOREIGN PATENT DOCUMENTS

| EP | 0100769 A1 | 2/1984 |
| WO | WO 97/10868 | 3/1997 |
| WO | WO 99/47197 | 9/1999 |

*Primary Examiner*—Denise L. Esquivel  
*Assistant Examiner*—Malik N. Drake  
(74) *Attorney, Agent, or Firm*—Townsend and Townsend and Crew LLP

(57) ABSTRACT

A gas forwarding apparatus for respiration and narcosis devices including a radial compressor and a drive apparatus which produces a magnetic rotary field, with the radial compressor including a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus.

39 Claims, 13 Drawing Sheets

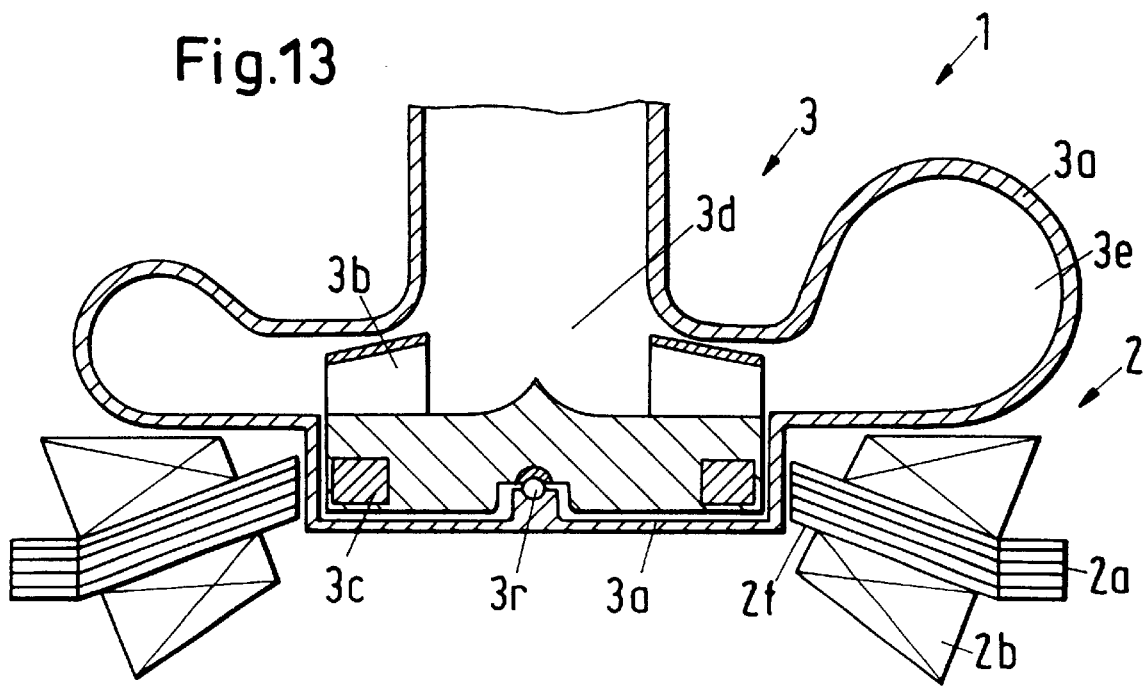
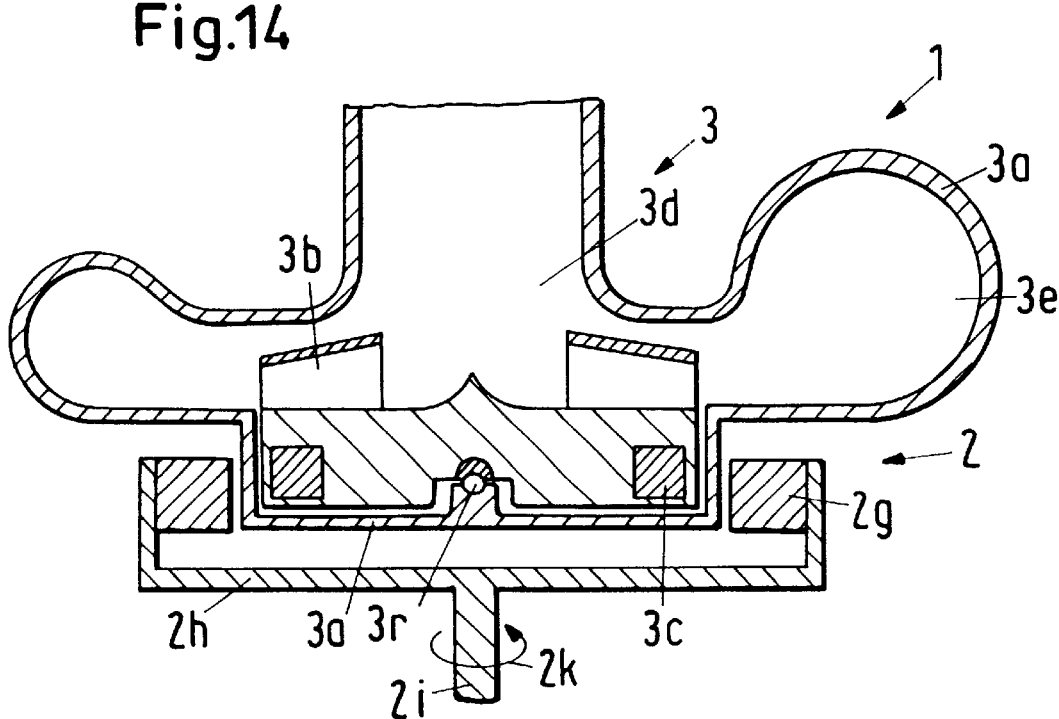

GAS FORWARDING APPARATUS FOR RESPIRATION AND NARCOSIS DEVICES

BACKGROUND OF THE INVENTION

The invention relates to a gas forwarding apparatus for respiration and narcosis devices.

A gas forwarding apparatus for respiration and narcosis devices is known from the specification DE 197 14 644 A1. This gas forwarding apparatus comprises a radial compressor with backwardly curved blades. The radial compressor is electrically driven and also permits an intermittent respiration in that the speed of rotation of the radial compressor is correspondingly modulated. No additional pressure gas supply is required for the operation of this gas forwarding apparatus. This gas forwarding apparatus is suitable for narcosis devices or for respiration devices for the production of a continuous positive respiratory canal pressure, also designated as CPAP (Continuous Positive Air Pressure).

Disadvantageous in this known gas forwarding apparatus is that an electrical motor with a relatively high drive power is required for its operation. In addition it is very laborious to clean and disinfect the gas forwarding apparatus. A sterile gas forwarding apparatus is in particular of central importance when a patient is respirated through intubation. In particular in an endo-trachial intubation the risk of a pneumonia is considerably increased, with the latter being caused above all by bacteria. Therefore it is of central importance for the respiration and narcosis devices and in particular also a possibly used humidifier system to be free of bacteria.

SUMMARY OF THE INVENTION

It is an object of the present invention to propose a gas forwarding apparatus for respiration and narcosis devices which is constructed simply and economically and which is in particular bacteriologically advantageous.

The object is satisfied in particular by a gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus.

The gas forwarding apparatus in accordance with the invention has the advantage that the radial compressor can be manufactured very economically and that the forwarded fluid is completely separate from the drive apparatus. In a preferred embodiment the radial compressor and the drive apparatus are designed to be mutually separable. This radial compressor is advantageously designed as a one-way product or as a throw-away product respectively. This has the advantage that the laborious cleaning process of the gas forwarding apparatus is omitted, since the radial compressor and advantageously also the remaining fluid conducting components are designed as one-way products. Thus it is ensured in addition that a newly used gas forwarding apparatus is sterile.

The object is also in particular satisfied by a gas forwarding apparatus for respiration and narcosis devices, comprising a radial compressor and a bypass, with the bypass forming a fluid conducting connection between the suction side and the compression side of the radial compressor. Thanks to this bypass the radial compressor can also be operated without forwarding power in that the fluid is rerouted via the bypass without the radial compressor or the drive motor respectively being damaged. In a preferred embodiment a controllable valve is arranged at the bypass which enables the cross-section of the bypass to be modulated, so that the fluid pressure which is produced by the radial compressor can be controlled via the valve.

The object is also in particular satisfied by a gas forwarding apparatus for respiration and narcosis devices, comprising a radial compressor with a housing as well as comprising a compressor wheel which is arranged within the housing and a rotor which is arranged within the housing and which is connected to the compressor wheel, with the housing and the rotor being designed to be matched with respect to a separate drive apparatus in such a manner that the rotor can be coupled to the drive apparatus and can be driven by the latter. This arrangement has the advantage that the gas forwarding apparatus is completely separate from the drive apparatus. The gas forwarding apparatus can be coupled to the drive apparatus. This gas forwarding apparatus is preferably designed as a one-way product.

In the following the invention will be explained in detail with reference to a plurality of exemplary embodiments.

BRIEF DESCRIPTION OF THE DRAWINGS

FIG. 13 is a longitudinal section through a further exemplary embodiment of a gas forwarding apparatus with a radial compressor, a step bearing and an electric motor; and FIG. 14 is a longitudinal section through a further exemplary embodiment of a gas forwarding apparatus with a radial compressor, a step bearing and a magnetic coupling.

DETAILED DESCRIPTION OF SPECIFIC EXEMPLARY EMBODIMENTS

Figure 1:
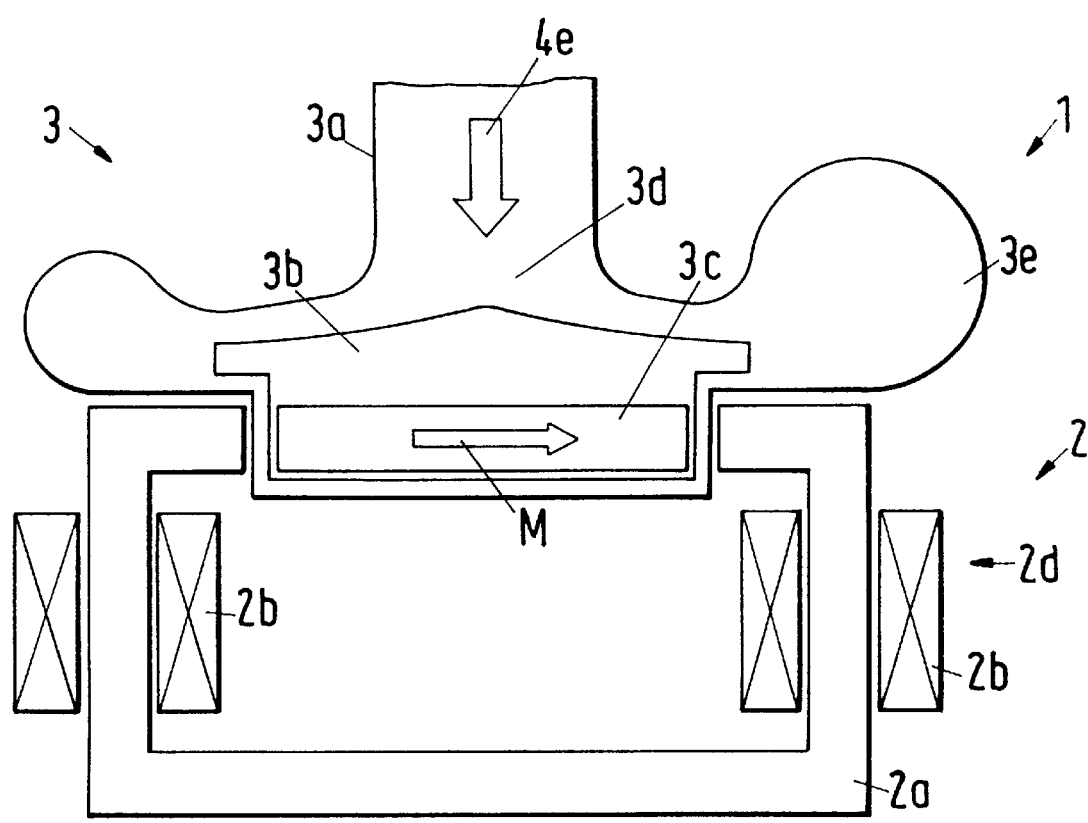
FIG. 1 is a longitudinal section through a gas forwarding apparatus with a radial compressor and a bearingless electric motor.

FIG. 1 shows a gas forwarding apparatus 1 comprising a drive apparatus 2 and a radial compressor 3. The radial compressor 3 comprises a housing 3a within which a compressor wheel 3b with non-illustrated blades is arranged, with a motor rotor 3c which is designed as a permanent magnet and which has a magnetization M also being cast into the compressor wheel 3b, which consists of plastic. The radial compressor 3 has a gas inlet 3d or a suction side 3d respectively and a gas outlet 3e or a compression side 3e respectively, so that a gas flow 4e arises during the operation of the radial compressor 3. The radial compressor 3 is releasably connected to the motor stator 2d which is arranged below it. The motor stator 2d forms together with the motor rotor 3c an electric motor, with the electric motor being designed as a bearingless motor. A bearingless motor of this kind is for example disclosed in the specification EP 0 819 330. The motor stator 2d comprises a sheet metal lamina package consisting of soft iron 2a, into the grooves of which a motor winding is inserted which can be excited by a non-illustrated controller apparatus in such a manner that a rotary field or an alternating field with a first number of pole pairs p is produced, so that the permanent magnet 3c, which is likewise magnetized with the number of pole pairs p in the peripheral direction, and thereby also the compressor wheel 3b, is driven in the peripheral direction. The motor winding 2b is furthermore designed in such a manner that in addition a rotary field with a second number of pole pairs p+1 or p−1 develops. This rotary field is regulated in such a manner that the permanent magnet 3c with the compressor wheel 3b is held without contact in the radial direction. The permanent magnet 3c, and thus also the compressor wheel 3b, is held in a stable position in the axial direction and against tilting through passive magnetic forces. As indicated in FIG. 1, the radial compressor 3 can be inserted into the motor stator 2d and also removed from it in a simple way. This is achieved in that the motor stator 2d is designed as a so-called temple motor. In a preferred embodiment the housing 3a and the compressor wheel 3b are designed to be of plastic and are conceived as a throw-away product or as a one-way product respectively. This arrangement in accordance with the invention enables the motor stator 2d to be reused, whereas the radial compressor 3 is preferably used only once and then disposed of. This radial compressor 3 can be manufactured very economically, since in a simple embodiment it comprises in addition to the likewise very economical permanent magnet 3c only the housing 3a and the compressor wheel 3b.

This arrangement in accordance with the invention has in particular the advantage that the radial compressor 3 is conceived as a throw-away product and thus requires no cleaning, so that in each use of the respiration or narcosis device there is the certainty that the radial compressor 3 is initially in a sterile state.

The gas forwarding apparatus 1 in accordance with the invention has the additional advantage that the compressor wheel 3b has a very low mass, and that the compressor wheel 3b is held without contact in the radial compressor 3 through the drive apparatus 2, which is designed as a bearingless motor. This enables on the one hand a very high speed of rotation of the compressor wheel 3b as well as a rapid speed of rotation variation of the compressor wheel 3b. This enables a high speed of rotation or pressure change respectively to be achieved within a few milliseconds via a corresponding excitation of the motor windings 2b. Thus pressure changes or breathing patterns respectively can be produced through a corresponding modulation of the speed of rotation of the compressor wheel 3b.

A further advantage of the illustrated motor is that the compressor wheel 3b has a low mass, that the compressor wheel 3b is journalled without contact, and that a low electrical power is therefore required for its operation. This enables a gas forwarding apparatus in accordance with the invention also to be operated with a battery and thus to be designed as a portable or mains-independent gas forwarding apparatus 1. This is of central importance in particular in its use for respiration devices in order to use the gas forwarding apparatus 1 as a portable device or for example in the home field as a small, easy to handle device.

FIG. 2 again shows a gas forwarding apparatus 1 with a drive apparatus 2 and a radial compressor 3 which is journalled and driven without contact. Within the housing 3a the compressor wheel 3b is connected via a spigot-like extension to a permanent magnet 3c and two magnetic bearing rotors 3f, 3g. The two radial magnetic bearing stators 2c, 2e, which are arranged to be vertically displaced, form together with the magnetic bearing rotors 3f, 3g in each case an active radial bearing. The magnetic bearing rotors 3f, 3g are designed as a package of sheet metal lamina. The motor stator 2d with motor windings 2b and sheet metal lamina package 2a forms together with the motor rotor 3c an electric motor which drives the compressor wheel 3b. The arising reluctance forces exert a passively acting force in the vertical direction, so that the compressor wheel 3b is also held without contact in the vertical direction.

Figure 2:
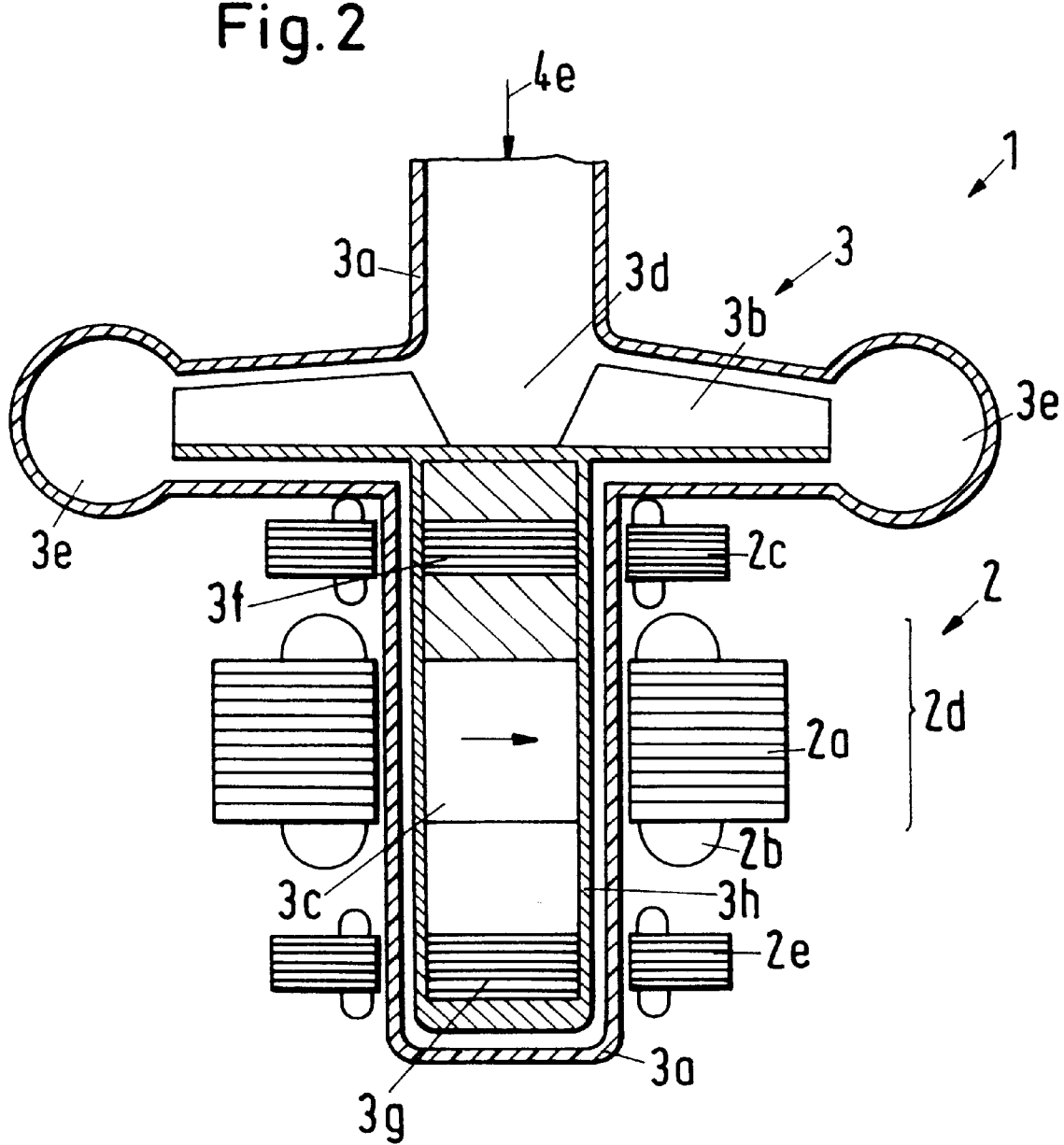
FIG. 2 is a longitudinal section through a further exemplary embodiment of a gas forwarding apparatus with a radial compressor, two active radial bearings and an electric motor.
Figure 3:
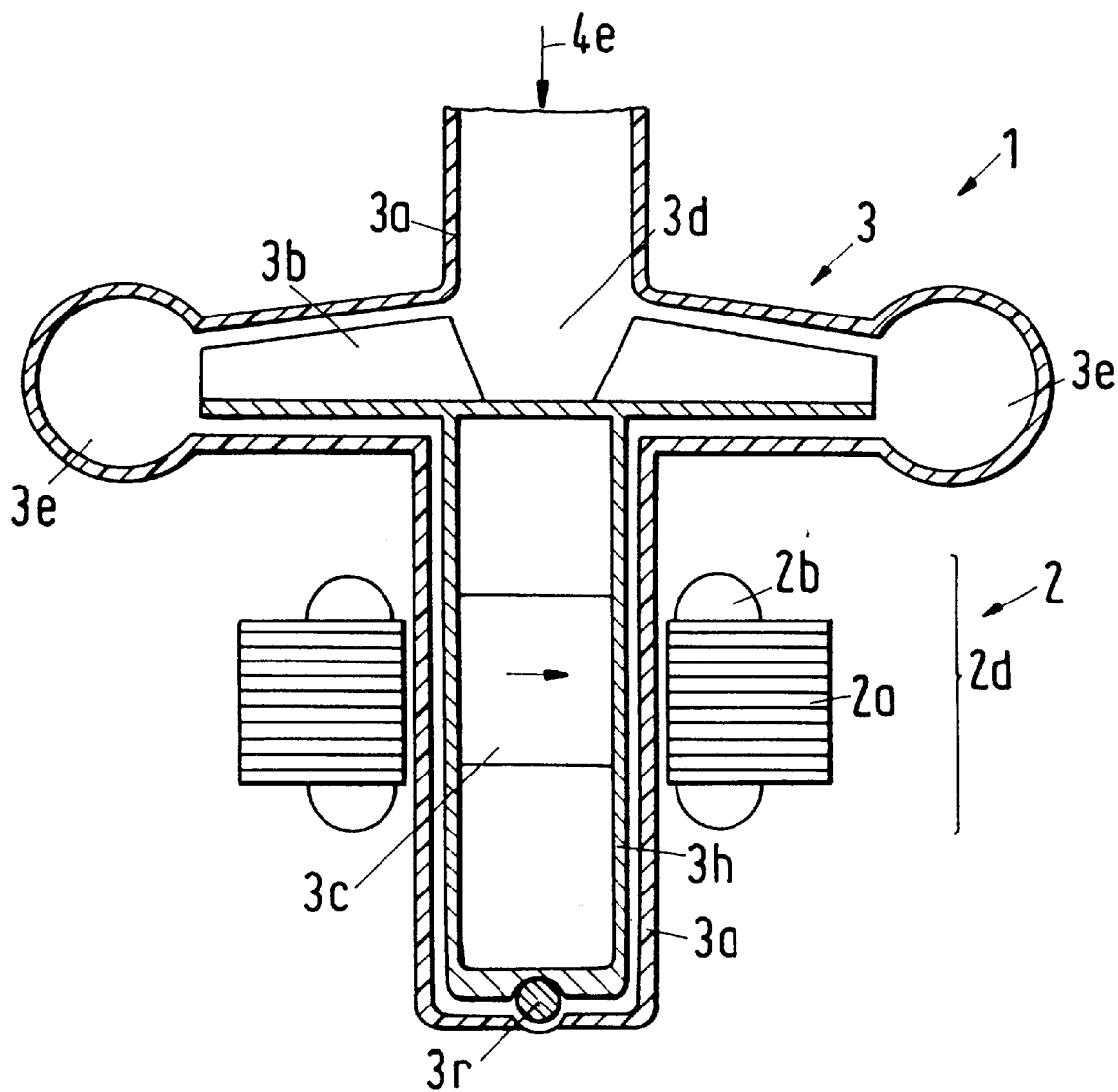
FIG. 3 is a longitudinal section through a further exemplary embodiment of a gas forwarding apparatus with a radial compressor, a step bearing and a bearingless electric motor.

FIG. 3 shows a further exemplary embodiment of a gas forwarding apparatus 1. It comprises a drive apparatus 2 and a radial compressor 3. In contrast to the exemplary embodiment which is illustrated in FIG. 2 the drive apparatus 2 comprises only the bearingless electric motor with the motor rotor 3c and the motor stator 2d, with a magnetic rotary field being produced in the motor stator 2d through a corresponding excitation of the coils 2b in order to set the permanent magnetic armature 3c rotating and to radially magnetically journal it. Naturally the motor rotor can also be designed as an induction motor armature or as a reluctance motor armature. In the vertical direction the compressor wheel 3b is supported and guided in the vertical direction by a step bearing 3r which is arranged below in the housing 3a. Through this the rotor is stabilized both in the axial direction and against tilting. The motor stator 2d is slightly downwardly displaced relative to the motor rotor 3c in order to produce a slight vertically downwardly directed magnetic force.

Figure 4:
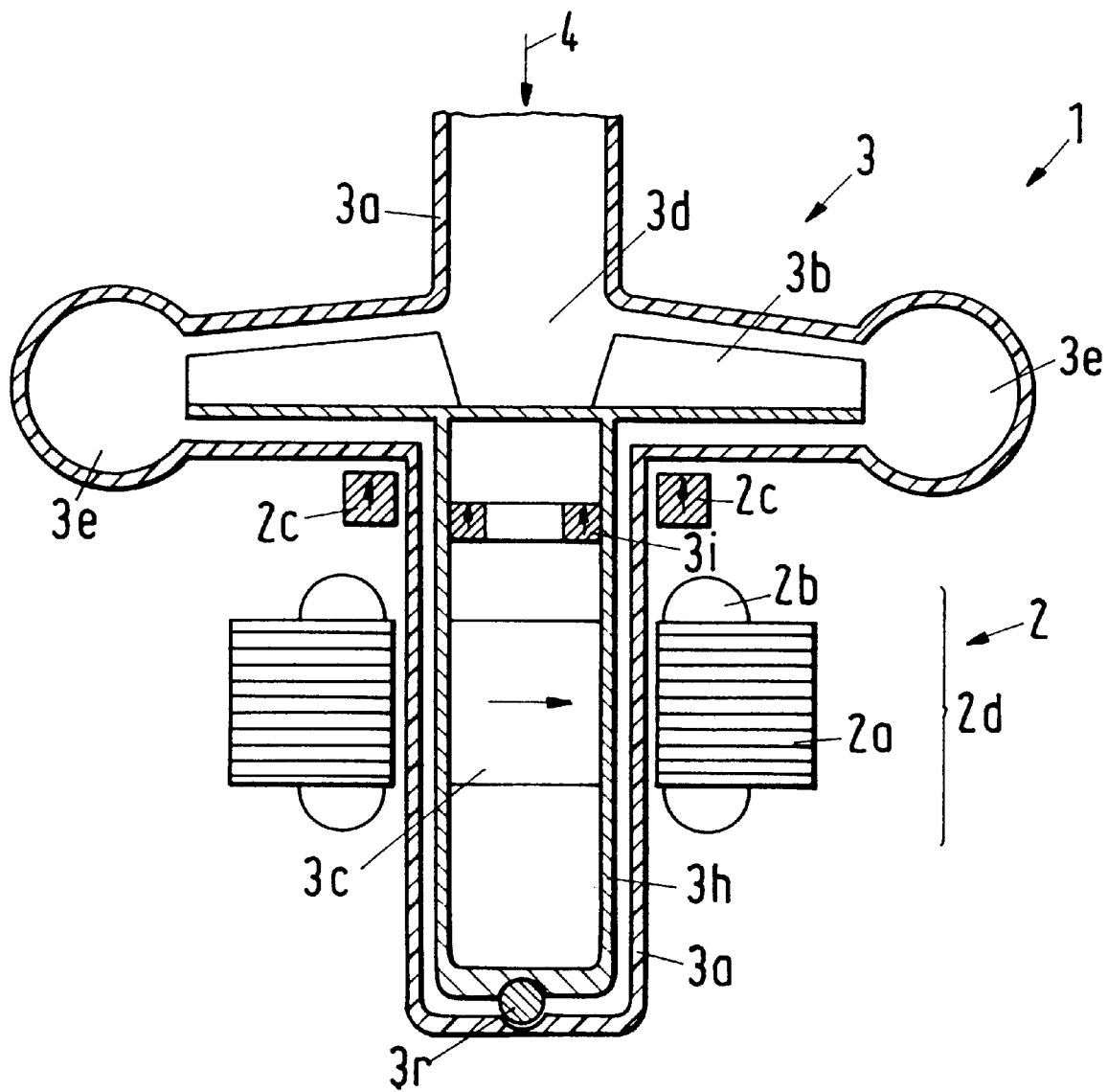
FIG. 4 is a longitudinal section through a further exemplary embodiment of a gas forwarding apparatus with a radial compressor, a step bearing, a passive radial bearing and an electric motor.

In addition to the embodiment which is illustrated in FIG. 3 the gas forwarding apparatus 1 which is illustrated in FIG. 4 has a passive radial magnetic bearing comprising a permanent magnet ring 2c which is arranged outside the housing 3a and a permanent magnet ring 3i which is firmly connected to the compressor wheel 2b. Since the passive radial magnetic bearing already effects a radial guiding of the rotor 3c, a conventional electric motor which merely drives the rotor 3c can be used instead of a bearingless electric motor. In particular the control electronics for the motor stator 2d can thereby be considerably simplified. The permanent magnet ring 2c, which is arranged outside the housing 3a and which forms the magnetic bearing stator of the passive radial magnetic bearing, is arranged to be vertically slightly upwardly displaced relative to the permanent magnet ring 3*i*, which is firmly connected to the compressor wheel 2*b* and which forms the magnetic bearing rotor. A slight vertically downwardly directed magnetic force thereby acts on the rotor, which is taken up by the step bearing 3*r*. The rotor is thus firmly axially held in both directions.

Figure 5:
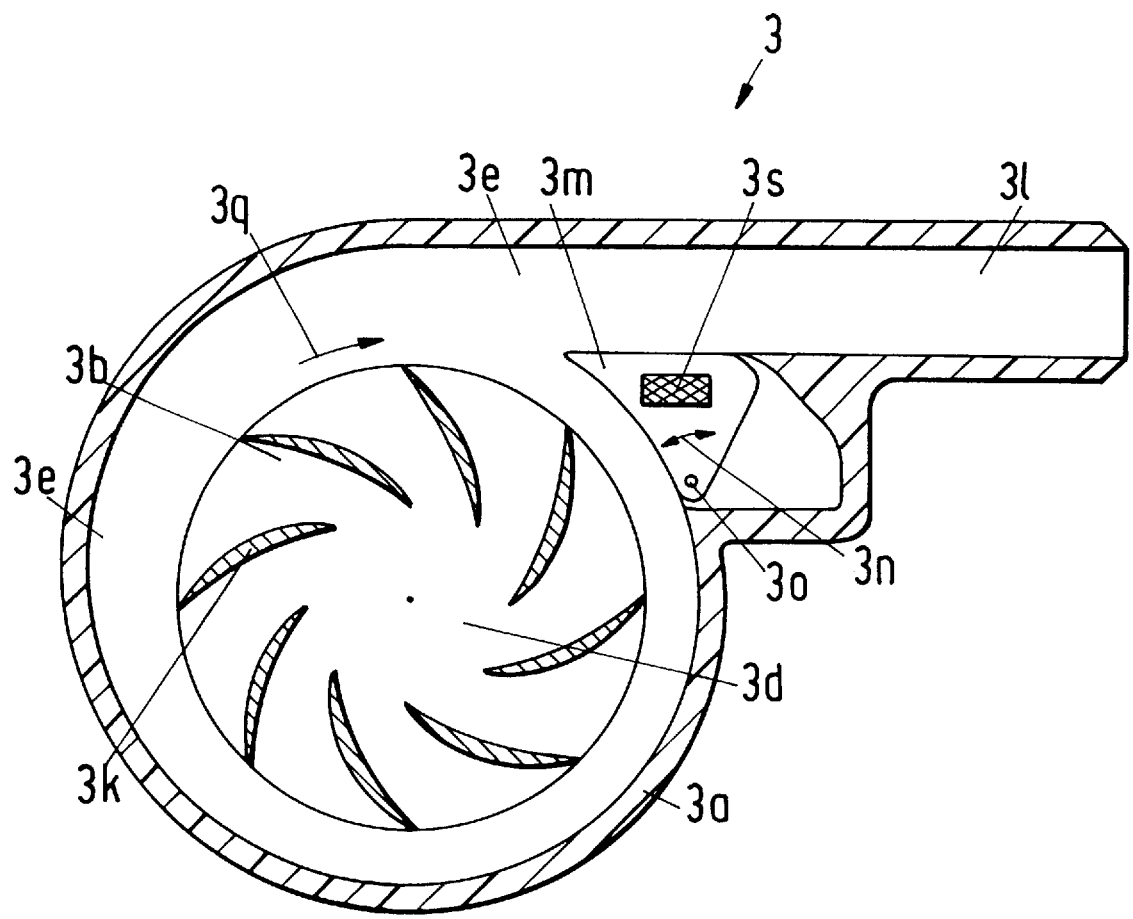
FIG. 5 is a cross-section through a radial compressor with an opened valve.

FIG. 5 shows a cross-section through a radial compressor 3. A compressor wheel 3*b* with blades 3*k* is journalled inside the housing 3*a* so as to be rotatable in the direction of rotation 3*q*. The forwarded fluid enters via the gas inlet 3*d* or the suction side 3*d* respectively into the compressor wheel 3*b* and is then forwarded to the gas outlet 3*e* or to the compression side 3*e* respectively and then arrives at the gas outlet 31. A valve 3*m* which is designed in the shape of a tongue and which is rotatably journalled about a center of rotation 3*o* in the direction of movement 3*n* is arranged ahead of the gas outlet 31. In addition a permanent magnet 3*s* is arranged in the tongue 3*m*.

Figure 6:
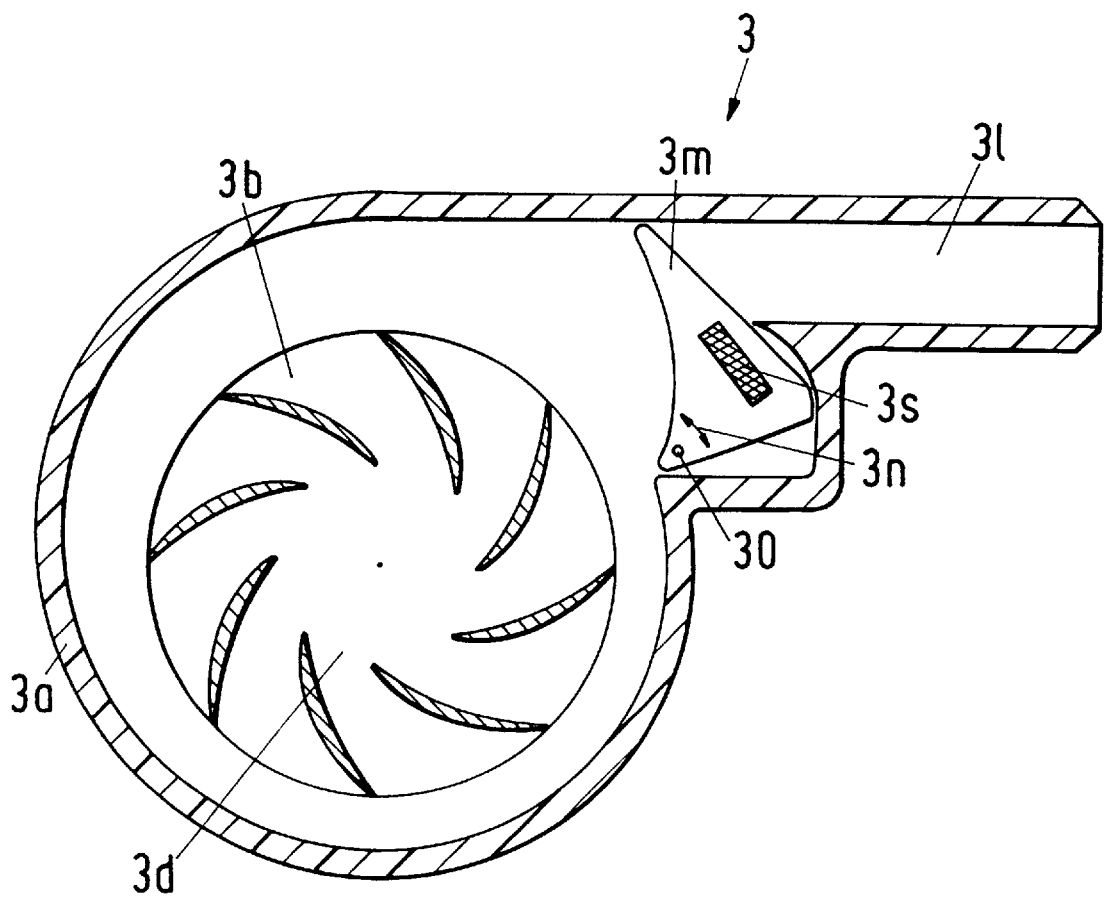
FIG. 6 is a cross-section through a radial compressor with a closed valve.

FIG. 6 shows a cross-section through a radial compressor 3 with closed valve 3*m*. In this position the fluid which is located in the radial compressor 3 is circulated without entering into the gas outlet 31 in the process. A non-illustrated, movable permanent magnet which acts on the permanent magnet 3*s* of the tongue 3*m* is arranged outside the housing 3*a*, so that the tongue 3*m* is movable without contact. The position of the permanent magnet which is located outside the housing is regulated via a setting member. The position of the valve 3*m* can thereby be controlled and thus the gas pressure at the gas outlet 31 or the volume flow respectively can be influenced. In the open valve position, shown in FIG. 5, the gas pressure or the volume flow respectively is a maximum and is determined at a given speed of rotation by the restrictor curve of the blower and by the flow resistance of the entire respiration system inclusive of the catheter, air tube, lung, etc. In the closed position, shown in FIG. 6, the gas pressure at the gas outlet 31 and the volume flow is a minimum, in practice nearly 0. Through variation of the valve position the gas pressure at the gas outlet 31 or the volume flow respectively can thus be set. Through temporal variation of the valve position almost any desired respiration pattern can be produced. In combination with a pressure sensor or a volume flow sensor respectively, pressure courses or volume flow courses respectively can be regulated very precisely.

Figure 7:
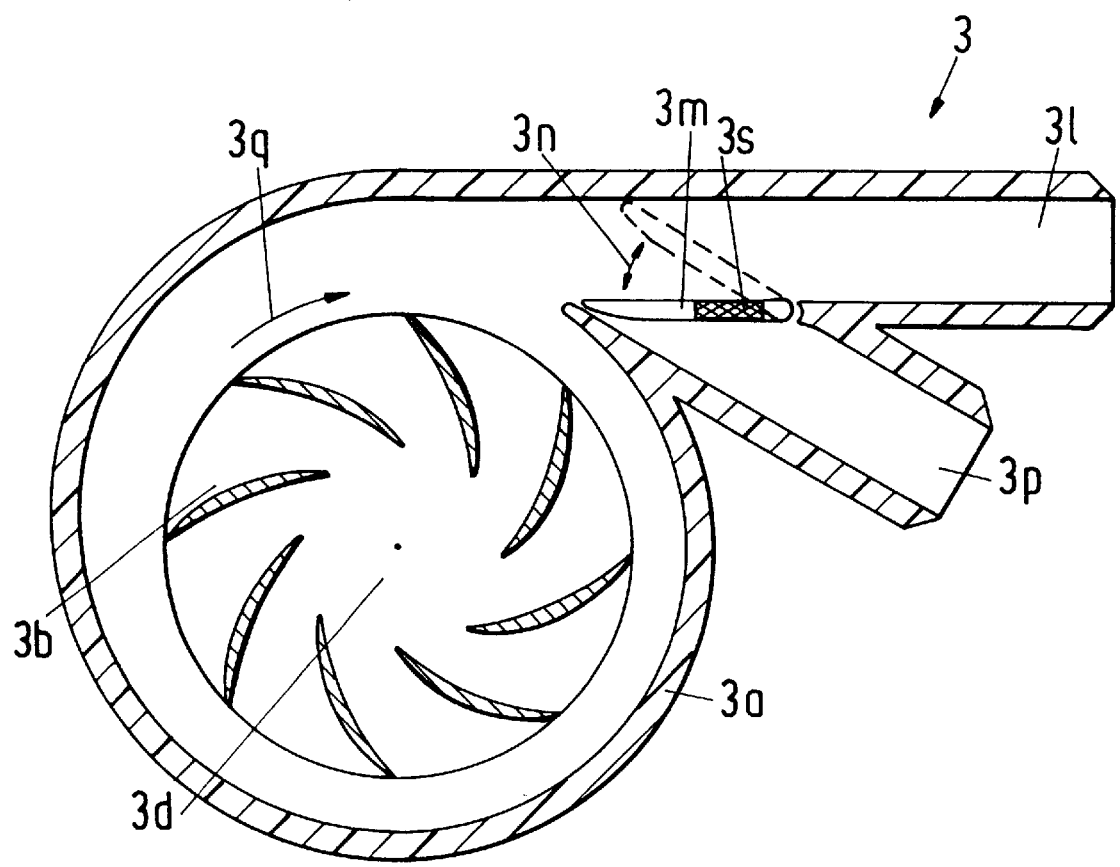
FIG. 7 is a cross-section through a radial compressor with a further embodiment of a valve.

FIG. 7 shows a cross-section through a further exemplary embodiment of a radial compressor 3. This radial compressor 3 has two gas outlets 31, 3*p*, with the tongue, 3*m*, which is pivotally journalled in the direction of movement 3*n*, with permanent magnet 3*s* controllably supplying the fluid which is forwarded by the radial compressor 3 at least partly to the gas outlet 31 and/or to the gas outlet 3*p*. The gas outlet 31 is for example connected via a hose system to a respiration mask or a respiration catheter, whereas the gas outlet 3*p* is led back via a bypass hose to the gas inlet 3*d* or is conducted to the ambient air via a bacteria filter. Again through variation of the valve position almost any desired respiration patterns can be produced.

Figure 8:
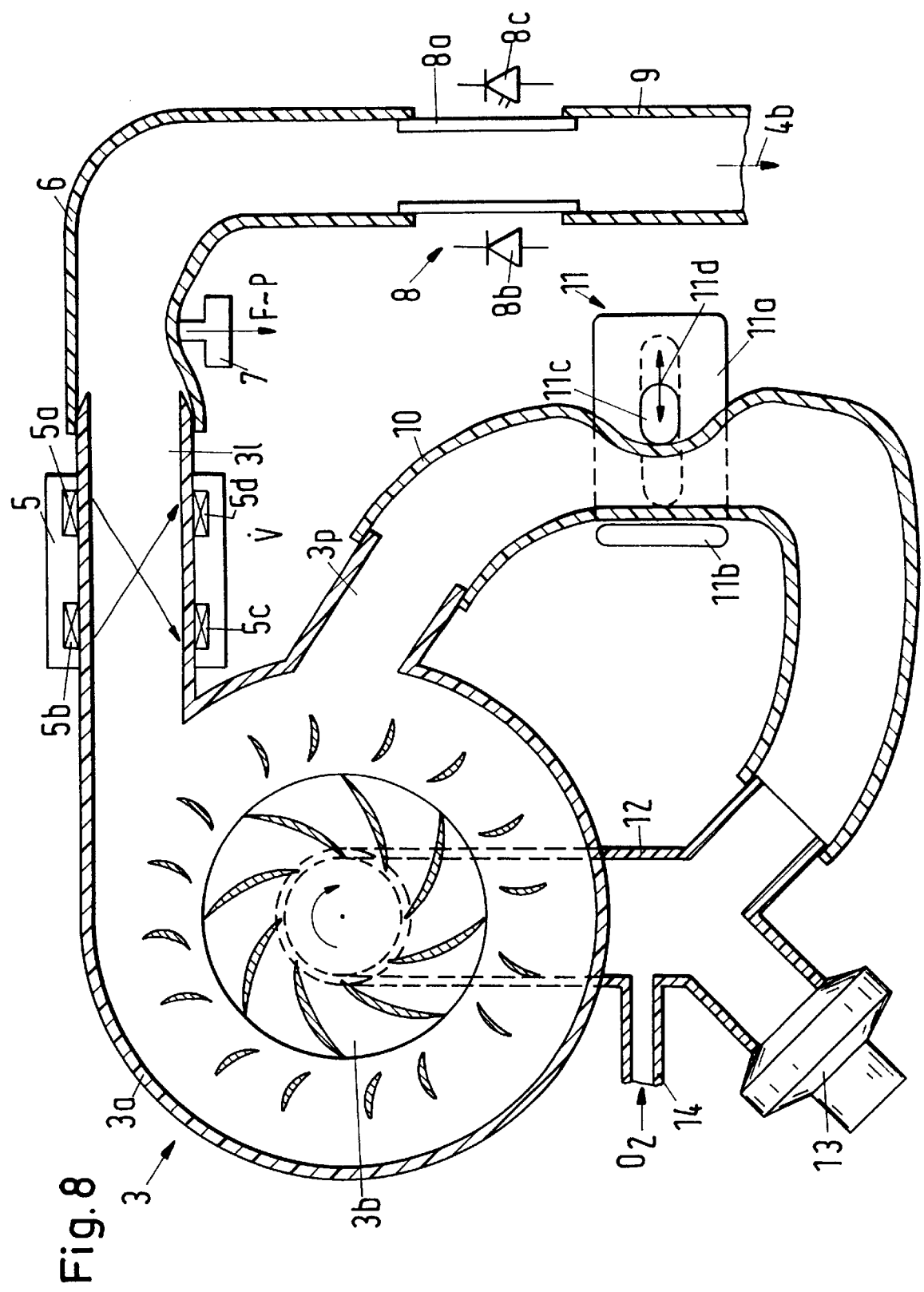
FIG. 8 illustrates schematically a gas forwarding apparatus with a radial compressor and further components which are connected up to the radial compressor.

FIG. 8 shows a gas forwarding apparatus 1 comprising a radial compressor 3 and a plurality of components which are connected thereto. The radial compressor 3 has a first gas outlet 31, about which a volume flow measurement apparatus 5 with two ultrasonic transmitters 5*a*, 5*b* and two ultrasonic receivers 5*c*, 5*d* is arranged in order to measure the volume flow of the fluid which flows through the gas outlet 31. An elastic hose 6 is arranged after the first gas outlet 31 and opens into a light-permeable tube 8*a*, with an elastic hose 9 again being arranged to follow. A pressure measurement apparatus 7 having a pressure sensor is arranged at the elastic hose 6 in order to measure the pressure P of the fluid which is located within the elastic hose 6. The light-permeable tube 8*a* forms part of a gas sensor 8, which comprises a photo-sensor 8*b* with a filter and a light source 8*c*, which is designed for example as an LED or as a laser diode. The three above-named sensors 5, 7 and 8 thus enable the volume flow, the pressure and the gas composition of the forwarded fluid to be measured.

The radial compressor 3 comprises a second gas outlet 3*p*, which opens via an elastic hose 10 into the line 12 and following that again into the gas inlet 3*d* of the radial compressor 3. The elastic hose 10 thus forms a bypass. In a preferred embodiment the amount of the fluid which flows through the bypass 10 can be regulated. In the illustrated exemplary embodiment a bypass regulation valve 11 is arranged at the bypass 10 and is designed as a linear actuator 11*a*, comprising a hose guide 11*b* and a closure piece 11*c* which is linearly movable in a direction of movement 11*d* and which enables the elastic hose 10 to be squeezed, which reduces the cross-section of the elastic hose 10. In addition a bacteria filter 13 for fresh air and an oxygen supply 14 are arranged at the line 12.

The embodiment illustrated in FIG. 8 has the property that slow pressure fluctuations for example with a slew rate of less than 200 millibar per second can be produced through a corresponding speed of rotation variation of the compressor wheel 3*b*. Rapid pressure fluctuations with a slew rate of more than 200 millibar per second are preferably produced in that the bypass regulation valve 11 is correspondingly controlled. Through a combination of speed of rotation variation and setting of the bypass regulation valve almost all known respiration patterns can be produced. In particular in combination with a pressure sensor 7 and/or a volume flow sensor 5 pressure profiles or volume flow profiles respectively can be regulated precisely. A further advantage of the embodiment which is illustrated in FIG. 8 is to be seen in that all components within which the fluid is forwarded, which comprise for example the radial compressor 3, the elastic hose 6, the light-permeable tube 8*a*, the elastic hose 9, the bypass 10 and the line 12 with fresh air filter 13, can be manufactured of a plastic, and that all these components contain no expensive objects such as sensors. In a preferred embodiment these fluid conducting components are therefore conceived as one-way product or a throw-away product respectively. These components are designed in such a manner that the radial compressor 3 can be introduced into the motor stator 2 in a simple way and the remaining components can be laid-in into the volume flow measurement apparatus 5, the pressure measurement apparatus 7, the gas determination sensor 8 and the bypass regulation valve 11 in a simple way. These expensive apparatuses, sensors and valves can be used again, with their also being protected against a bacteriological contamination since the fluid conducting system, which consists of plastic, is sealed off against the outside.

A further advantage of the gas forwarding apparatus 1 which is illustrated in FIG. 8 is to be seen in that a so-called "coughing through" is possible from the direction of the elastic hose 9, which means that a fluid conducting connection with low flow resistance is continuously present between the elastic hose 9 and an outlet, in the illustrated example the filter 13. The gas volume change which is almost abruptly produced by a patient by a cough is not substantially hindered within the gas forwarding apparatus 1, but can propagate through the blower and relaxes via the filter 13 without a painful or even dangerous pressure rise coming about in the lung.

Figure 9:
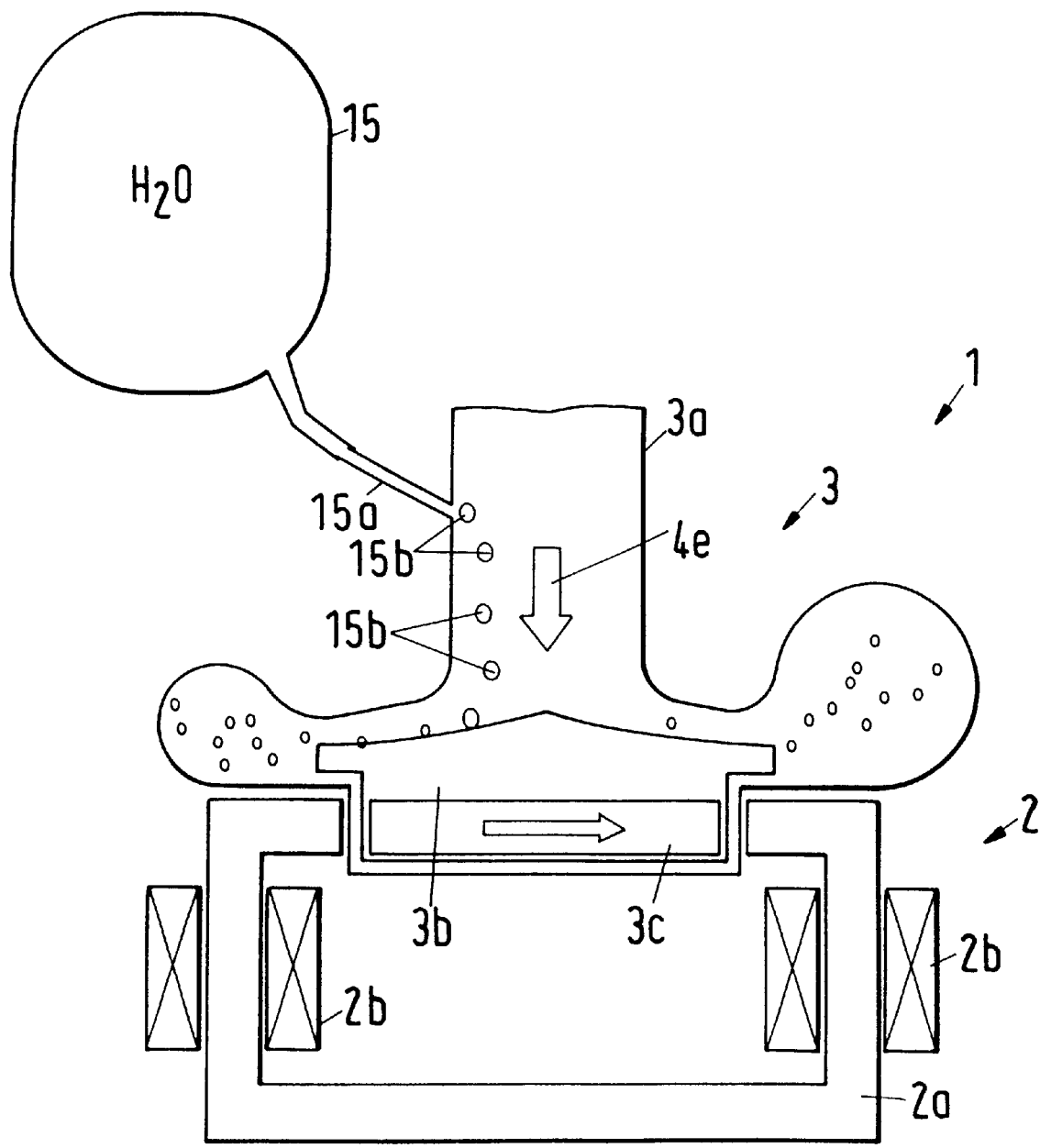
FIG. 9 is a longitudinal section through the arrangement in accordance with FIG. 1 with an additional infeed for humidifying the air.

In addition to the gas forwarding apparatus 1 which is illustrated in FIG. 1, the exemplary embodiment which is illustrated in FIG. 9 comprises a liquid container 15, in particular for water, with the liquid container 15 opening via an infeed line 15a above the compressor wheel 3b into the housing 3a of the radial compressor 3. The liquid drops 15b which form inside the housing 3a fall onto the compressor wheel 3b, which rotates at a high speed of rotation of for example 30,000 revolutions per minute, with the liquid drops 15b being atomized in the finest manner as a result of the high speed of rotation, so that the gas flow 4e is humidified in the radial compressor 3.

Figure 10:
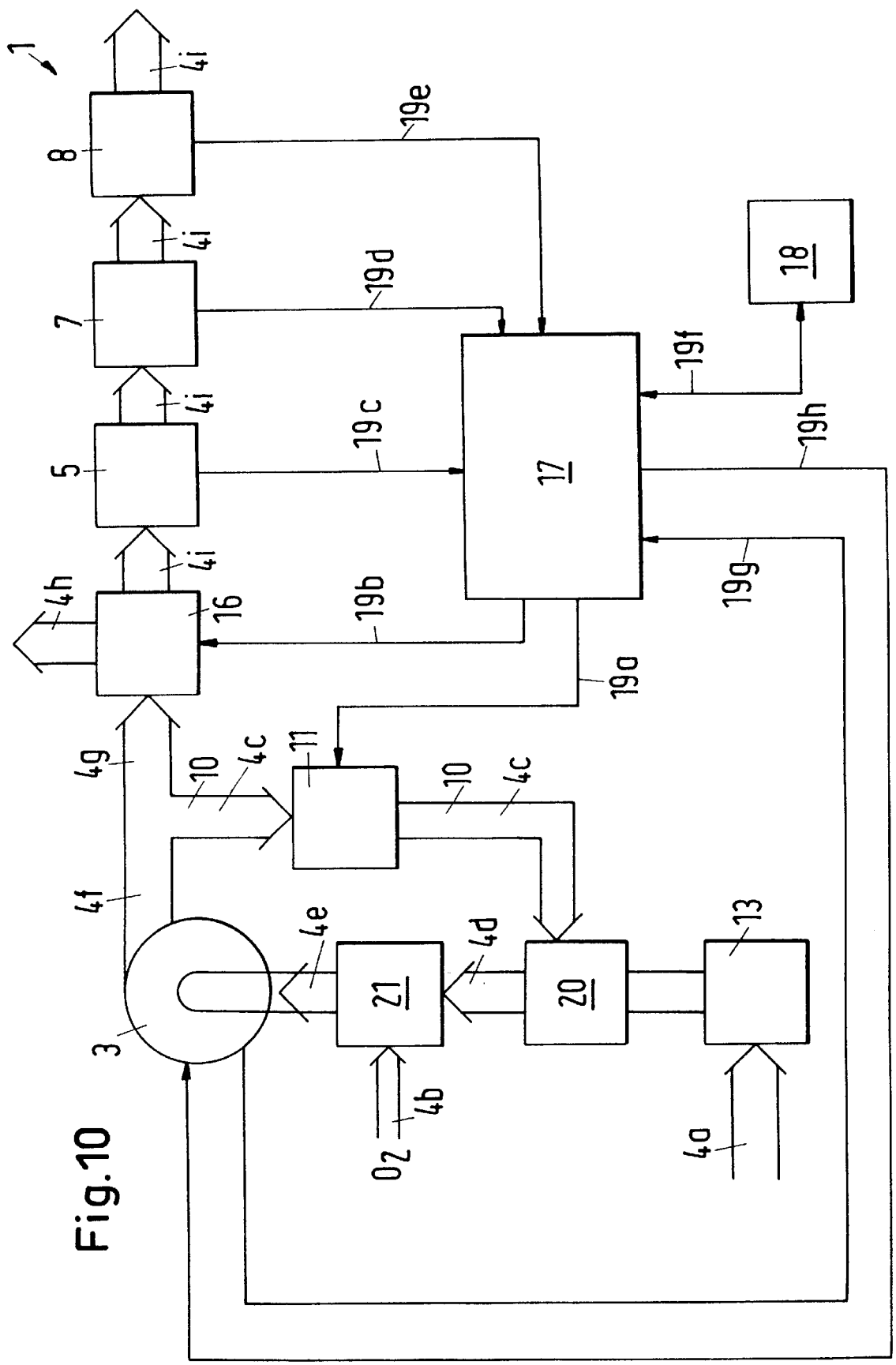
FIG. 10 is a schematic illustration of the individual components of the gas forwarding apparatus which are provided for a respiration device.

FIG. 10 shows a comprehensive exemplary embodiment of a gas forwarding apparatus 1, which is suitable for a respiration device or narcosis device. The fresh air 4a is sucked in via a filter 13 and enters via the storage volume 20 as a gas flow 4d into the coupling piece 21, in which also an oxygen gas flow 4b, other respiration gases or narcosis gas are admixed. This mixture is sucked in by the radial compressor 3 as a gas flow 4e and is further forwarded as a gas flow 4f, with a portion of this gas flow being supplied as a bypass gas flow 4c via the bypass 10 and the bypass regulation valve 11 to the storage volume 20, whereas the other portion of the gas flow 4f is supplied as a gas flow 4g or 4i respectively to the patient for assistance in respiration. In the exhalation valve 16 there is arranged a valve which can be controlled via the control apparatus 17 and which detours the fluid flow 4i on exhalation in such a manner that an exhalation gas flow 4h arises. Placed after the exhalation valve 16 is a volume flow measurement apparatus 5, then a pressure measurement apparatus 7 and then a gas determination sensor 8. The bypass regulation valve 11, the exhalation valve 16, the volume flow measurement apparatus 5, the pressure measurement apparatus 7 and the gas determination sensor 8 are connected via electrical lines 19a, 19b, 19c, 19d, 19e in a signal conducting manner to the control apparatus 17. In addition an input/output apparatus 18 is provided which is likewise connected to the control apparatus 17 via an electrical line 19f. In addition the control apparatus 17 is connected via electrical lines 19g, 19h to the radial compressor 3 in order to regulate its speed of rotation and to measure or to monitor its speed of rotation or its state respectively.

Figure 11:
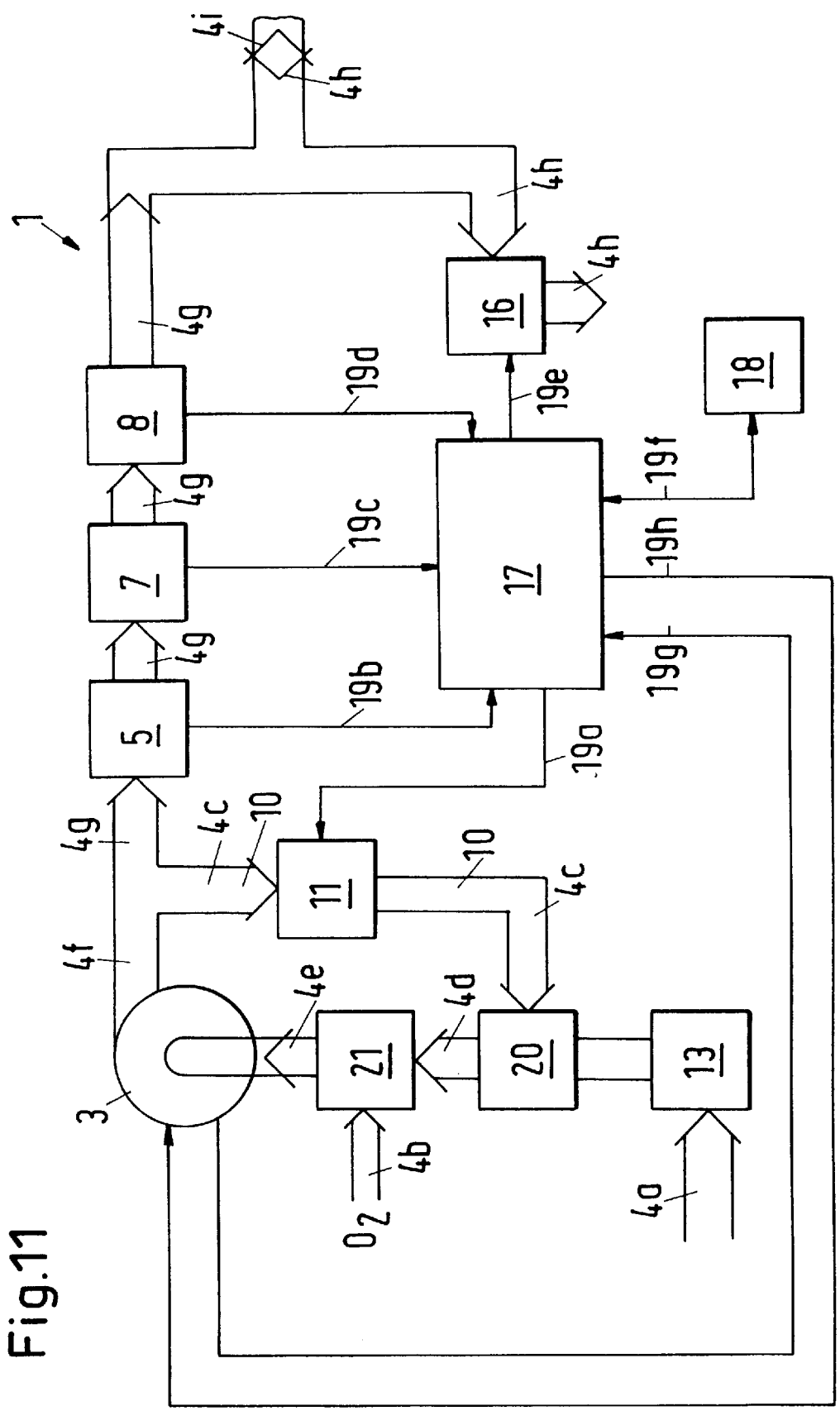
FIG. 11 is a further schematic illustration of the individual components for a respiration or narcosis device.

FIG. 11 shows in a schematic illustration a further gas forwarding apparatus 1 which is designed for use as a respiration and narcosis device. In contrast to the embodiment which is illustrated in FIG. 10, in the gas forwarding apparatus 1 in accordance with FIG. 11 the exhalation valve 16 is not arranged in the gas flow 4g but rather in a separate path, so that the exhalation gas flow 4h is conducted via the exhalation valve 16, with the exhalation valve 16 being controlled in such a manner by the control apparatus 17 that it is open during the exhalation phase of the patient.

In a preferred embodiment the fluid conducting conduction means are designed as one-way products or throw-away products in the gas forwarding apparatuses 1 which are illustrated in FIGS. 10 and 11, with these throw-away products preferably also comprising the radial compressor 3. These throw-away components are designed such that they can be laid-in into the expensive components such as the bypass regulation valve 11, the volume flow measurement apparatus 5, the pressure measurement apparatus 7 or the gas determination sensor 8 or the exhalation valve 16.

Figure 12:
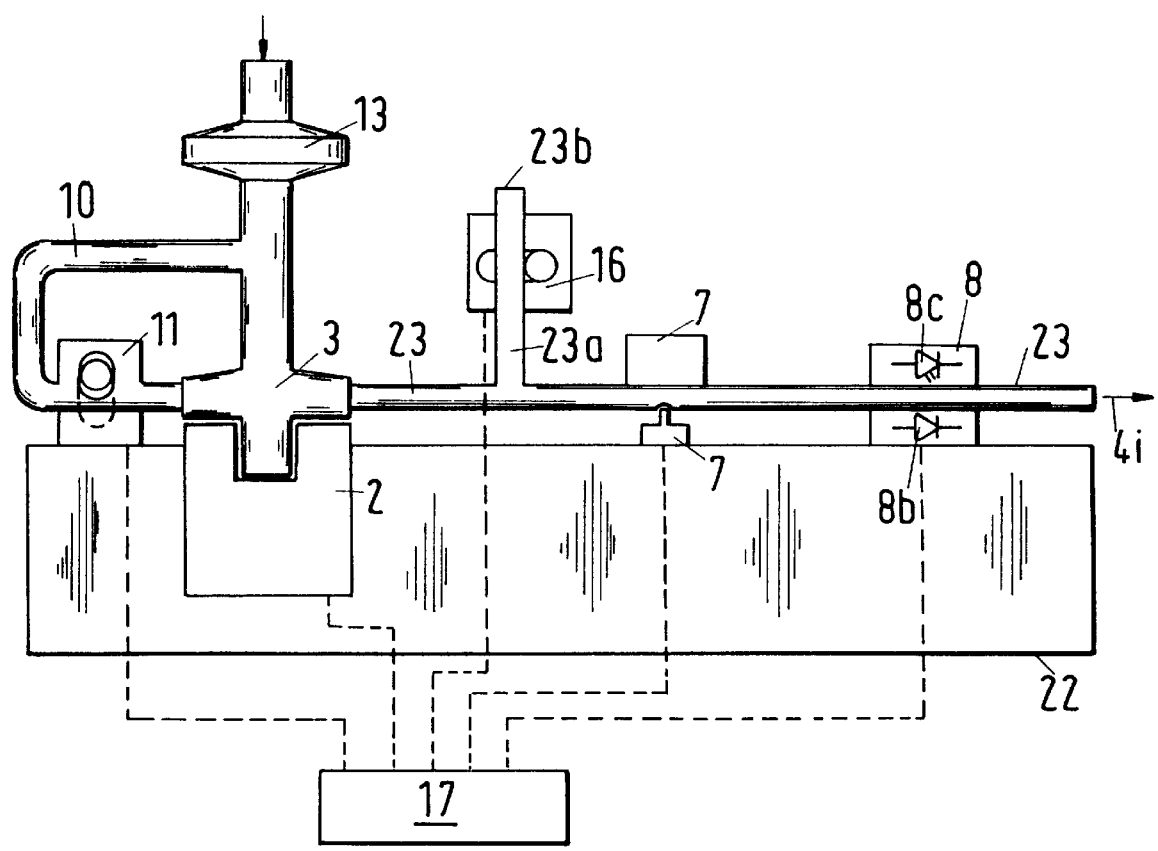
FIG. 12 illustrates schematically the arrangement of the individual components of a gas forwarding apparatus which is designed substantially as a one-way product.

FIG. 12 shows schematically an arrangement of this kind, with the gas compressor 3, the filter 13, the elastic hose 10, the elastic hose 23 and the branching 23a being designed to be connected, and for example also being designed in a single piece. These elements can be laid-in into the bypass regulation valve 11, into the motor stator 2, into the exhalation valve 16, the pressure measurement apparatus 7 and the gas determination sensor 8 in a very simple way. After this laying in the gas forwarding apparatus 1 is ready for operation and the individually controllable components can be controlled via the control apparatus 17. A substantial advantage of the arrangement which is illustrated in FIG. 12 is to be seen in that the fluid conducting components can be manufactured very economically and can therefore be conceived as one-way products or throwaway products respectively. It is therefore no longer necessary to sterilize the fluid conducting components in a laborious cleaning process. In each new use of a fluid conducting component it is ensured that the latter is sterile, which in particular considerably reduces the risk of a pneumonia in the intubation of a patient.

FIG. 13 shows in a longitudinal section a further exemplary embodiment of a gas forwarding apparatus 1. A compressor wheel 3b which is journalled on a step bearing 3r is arranged within the radial compressor 3. The compressor wheel 3b consists of plastic. A permanent magnet ring 3c or a plurality of permanent magnet segments 3c is arranged within the compressor wheel 3b. The motor stator 2 comprises a sheet metal lamina package 2a with motor windings 2b and stator teeth 2f. The motor stator 2 is arranged and designed with respect to the motor rotor 3c in such a manner that the projecting section 3b is journalled both in the radial direction and downwardly in the axial direction by the step bearing 3r, and is passively magnetically journalled upwardly in the axial direction and against a tilting.

FIG. 14 shows in a longitudinal section a further exemplary embodiment of a gas forwarding apparatus 1 comprising a radial compressor 3 and a drive apparatus 2 which is designed as a magnetic coupling. The compressor wheel 3b is journalled via a step bearing 3r in this exemplary embodiment, as in FIG. 13. To drive the compressor wheel 3b or the motor rotor 3c, which is designed as a permanent magnet, a circular magnetic coupling 2g which surrounds the compressor wheel 3b in the peripheral direction is provided and is driven in the direction of rotation 2k by a non-illustrated drive apparatus and is connected via the shaft 2i to the drive apparatus. The shaft 2i merges into a circular coupling 2h, at which a ring-shaped drive magnet 2g is arranged. The drive magnet 2g can also consist of a plurality of permanent magnet segments. The magnetic coupling 2g is arranged and designed with respect to the motor rotor 3c in such a manner that the compressor wheel 3b is journalled in the radial direction and downwardly in the axial direction by the step bearing 3r, and is journalled upwardly in the axial direction and against a tilting through the passive magnetic forces.

What is claimed is:

1. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the drive apparatus forms a magnetic bearing with the rotor; wherein at least one degree of freedom of the rotor is journalled by the magnetic bearing; and wherein the magnetic flux between the rotor and the drive apparatus is oriented mainly in a radial direction.

2. A gas forwarding apparatus in accordance with claim 1, wherein in that the drive apparatus and the rotor comprise an active radial bearing.

3. A gas forwarding apparatus in accordance with claim 1, wherein the drive apparatus is formed as a motor stator comprising a motor winding and an iron yoke, so that the motor stator drives the rotor.

4. A gas forwarding apparatus in accordance with claim 1, wherein the rotor comprises a permanent magnet.

5. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein a step bearing which rotatably journals the compressor wheel and the rotor with respect to the housing is arranged within the housing.

6. A gas forwarding apparatus in accordance with claim 5, wherein the drive apparatus comprises a rotatable magnetic coupling which can be arranged with respect to the rotor in such a manner that the rotating magnetic coupling drives the rotor.

7. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the motor stator together with the rotor is designed as a bearingless motor.

8. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the radial compressor and the drive apparatus are designed to be mutually separable; and wherein the radial compressor forms a unit which is separable from the drive apparatus and the drive apparatus drives the rotor contactlessly.

9. A gas forwarding apparatus in accordance with claim 8, wherein the radial compressor forms one of a disposable unit and a one way product.

10. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the radial compressor has in the region of the gas outlet a valve, designed as a displaceable tongue, in order at least partly to interrupt the gas flow.

11. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the valve is pivotally journalled and is movably journalled about a center of rotation.

12. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the valve comprises a permanent magnet; and wherein a drive apparatus which is designed to be correspondingly matched is arranged outside the radial compressor in order to move the valve via the permanent magnet.

13. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein a radial compressor has a first gas outlet and a second gas outlet.

14. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein a valve is arranged within the housing and is designed and is controllable in such a manner that the forwarded fluid is conveyed to at least one of the first and the second gas outlets.

15. A gas forwarding apparatus for respiration and narcosis devices, comprising a radial compressor and a drive apparatus which produces a magnetic rotary field, with the radial compressor comprising a housing within which a compressor wheel and a rotor which is connected thereto are arranged, with the drive apparatus being arranged outside the housing and with the drive apparatus and the rotor being designed to be mutually matched and arranged in such a manner that the rotor can be driven by the drive apparatus; wherein the housing has an opening which is arranged ahead of the compressor wheel in the flow direction and through which a liquid can be introduced.

16. A gas forwarding apparatus in accordance with claim 15 wherein the liquid is water.

17. A gas forwarding apparatus for respiration and narcosis devices, comprising a radial compressor and a bypass, with the bypass forming a fluid conducting connection between the suction side and the compression side of the radial compressor.

18. A gas forwarding apparatus in accordance with claim 17, wherein the bypass comprises a controllable valve.

19. A gas forwarding apparatus in accordance with claim 17, wherein the controllable valve is arranged in the region of the gas outlet of the radial compressor in such a manner that the gas flow is at least partly interruptible.

20. A gas forwarding apparatus in accordance with claim 19, wherein the controllable valve is designed to have the shape of a tongue and to be pivotal.

21. A gas forwarding apparatus in accordance with claim 17, wherein the bypass is designed to be elastic; and wherein the valve is designed as a bypass regulation valve which acts mechanically on the bypass in order to vary the inner cross-section of the bypass.

22. A gas forwarding apparatus in accordance with claim 21, wherein the bypass comprises an elastic hose.

23. A gas forwarding apparatus in accordance with claim 21, wherein the bypass regulation valve comprises a linearly driven closure part which acts mechanically on the bypass.

24. A gas forwarding apparatus in accordance with claim 17, further comprising a drive apparatus which is releasably connected to the radial compressor.

25. A method for a gas forwarding apparatus, for respiration and narcosis devices comprising a radial compressor and a bypass, with the bypass forming a fluid conducting connection between the suction side and the compression side of the radial compressor; wherein the speed of rotation of at least one of the radial compressor and the setting of the valve is varied in order to vary at least one of the static and dynamic pressures of the forwarded fluid.

26. A method in accordance with claim 25, wherein pressure fluctuations are produced in the forwarded fluid through a speed of rotation variation of the radial compressor.

27. A method in accordance with claim 25, wherein low frequency pressure fluctuations are produced via a speed of rotation variation of the radial compressor and higher frequency pressure fluctuations are produced via a variation of the setting of the valve.

28. A gas forwarding apparatus for respiration and narcosis devices, comprising a radial compressor with a housing and comprising a compressor wheel which is arranged within the housing and a rotor which is arranged within the housing and which is connected to the compressor wheel, with the housing and the rotor being designed to be mutually matched with respect to a separate drive apparatus in such a manner that the rotor can be coupled to the drive apparatus and can be driven by the latter; wherein a bypass forms a fluid conducting connection between a suction side and a compression side of the radial compressor.

29. A gas forwarding apparatus in accordance with claim 28, wherein the bypass is formed at least section-wise of an elastic material.

30. A gas forwarding apparatus in accordance with claim 29, wherein the bypass is formed as a hose.

31. A gas forwarding apparatus in accordance with claim 28, wherein the rotor is designed as a permanent magnet.

32. A gas forwarding apparatus in accordance with claim 28, wherein at least one of the housing and the compressor wheel consists of plastic.

33. A gas forwarding apparatus for respiration and narcosis devices, comprising a radial compressor with a housing and comprising a compressor wheel which is arranged within the housing and a rotor which is arranged within the housing and which is connected to the compressor wheel, with the housing and the rotor being designed to be mutually matched with respect to a separate drive apparatus in such a manner that the rotor can be coupled to the drive apparatus and can be driven by the latter; wherein the gas conducting section which follows the compression side of the radial compressor consists of plastic and is formed section-wise of an elastic material.

34. A gas forwarding apparatus in accordance with claim 29, wherein the radial compressor is formed as a hose.

35. A gas forwarding apparatus for respiration and narcosis devices, comprising a radial compressor with a housing and comprising a compressor wheel which is arranged within the housing and a rotor which is arranged within the housing and which is connected to the compressor wheel, with the housing and the rotor being designed to be mutually matched with respect to a separate drive apparatus in such a manner that the rotor can be coupled to the drive apparatus and can be driven by the latter; wherein at least the radial compressor is designed as a one way product or as a throw away product, respectively.

36. A gas forwarding apparatus in accordance with claim 35, wherein the gas forwarding apparatus comprises at least one of a volume flow measurement apparatus and a pressure measurement apparatus and the gas forwarding apparatus further comprises at least one of a volume flow measurement apparatus, a pressure measurement apparatus, a gas determination sensor and a drive apparatus for driving the magnetically active part, which are designed to be used a plurality of times.

37. A gas forwarding apparatus in accordance with claim 35, wherein at least one of the radial compressor and the gas conducting section is designed in such a manner that a releasable connection to at least one of the volume flow measurement apparatus and, the pressure measurement apparatus and, the gas determination sensor and the drive apparatus can be set.

38. A blower part of a gas forwarding apparatus, for respiration and narcosis devices comprising a radial compressor with a housing and comprising a compressor wheel which is arranged within the housing and a rotor which is arranged within the housing and which is connected to the compressor wheel, with the housing and the rotor being designed to be mutually matched with respect to a separate drive apparatus in such a manner that the rotor can be coupled to the drive apparatus and can be driven by the latter, the blower part consisting of a blower housing and a blower rotor which comprises a compressor wheel and a magnetically active rotor part, wherein the blower rotor is mechanically journalled in at most three spatial degrees of freedom.

39. A blower part in accordance with claim 38, wherein the blower rotor is freely movable in the blower housing with respect to all spatial degrees of freedom within the limits of the air gap.

* * * * *